(12) United States Patent
Abrahamson et al.

(10) Patent No.: US 10,316,338 B1
(45) Date of Patent: Jun. 11, 2019

(54) ENZYMATIC PROCESS FOR THE PREPARATION OF (1S,2R)-2-(DIFLUOROMETHYL)-1-(PROPOXYCARBONYL)CYCLOPROPANECARBOXYLIC ACID

(71) Applicant: AbbVie Inc., North Chicago, IL (US)

(72) Inventors: Michael J. Abrahamson, Chicago, IL (US); Angelica B. Kielbus, Evanston, IL (US); William T. Riordan, Libertyville, IL (US); David R. Hill, Gurnee, IL (US); Sanjay R. Chemburkar, Gurnee, IL (US); Rajarathnam E. Reddy, Gurnee, IL (US); Timothy B. Towne, Lindenhurst, IL (US); Jianzhang Mei, Lake Forest, IL (US); Gareth J. Brown, Antrim (GB); Stefan Mix, Belfast (GB)

(73) Assignee: Abb Vie Inc., North Chicago, IL (US)

( * ) Notice: Subject to any disclaimer, the term of this patent is extended or adjusted under 35 U.S.C. 154(b) by 334 days.

(21) Appl. No.: 15/010,557

(22) Filed: Jan. 29, 2016

Related U.S. Application Data

(60) Provisional application No. 62/109,943, filed on Jan. 30, 2015.

(51) Int. Cl.
   *C12P 7/62* (2006.01)
(52) U.S. Cl.
   CPC .................................... *C12P 7/62* (2013.01)

(58) Field of Classification Search
   None
   See application file for complete search history.

(56) References Cited

U.S. PATENT DOCUMENTS

| | | | |
|---|---|---|---|
| 9,809,534 | B1 | 11/2017 | Lukin et al. |
| 9,809,576 | B1 | 11/2017 | Cink et al. |
| 10,077,256 | B2 | 9/2018 | Cink et al. |
| 2015/0175626 | A1 | 6/2015 | Cagulada et al. |
| 2018/0057482 | A1 | 3/2018 | Cink et al. |
| 2018/0194721 | A1 | 7/2018 | Lukin et al. |

FOREIGN PATENT DOCUMENTS

WO  WO-2012/040167 A1  3/2012

OTHER PUBLICATIONS

U.S. Appl. No. 14/802,372, Cink et al.
U.S. Appl. No. 14/802,392, Lukin et al.

*Primary Examiner* — Paul J Holland
(74) *Attorney, Agent, or Firm* — Dana M. Gordon; Foley Hoag LLP

(57) ABSTRACT

Disclosed are methods of synthesizing enantioenriched difluoroalkylcyclopropyl amino esters and their salts, such as the dicyclohexylamine salt of (1S,2R)-2-(difluoromethyl)-1-(propoxycarbonyl)cyclopropane carboxylic acid. These compounds are useful intermediates in the synthesis of viral protease inhibitors.

13 Claims, No Drawings

Specification includes a Sequence Listing.

ENZYMATIC PROCESS FOR THE PREPARATION OF (1S,2R)-2-(DIFLUOROMETHYL)-1-(PROPOXY-CARBONYL)CYCLOPROPANECARBOXYLIC ACID

SEQUENCE LISTING

The instant application contains a Sequence Listing which has been submitted electronically in ASCII format and is hereby incorporated by reference in its entirety. Said ASCII copy, created on Mar. 18, 2016, is named AVR-034.01_SL.txt and is 1,631 bytes in size.

RELATED APPLICATION

This application claims the benefit of priority to U.S. Provisional Patent Application Ser. No. 62/109,943, filed Jan. 30, 2015, the contents of which is hereby incorporated by reference.

BACKGROUND

Complex biologically active molecules are challenging, expensive, and time-consuming to synthesize. Synthesizing chiral, non-racemic compounds with good enantio- and diastereoselectivity is even more challenging. Doing so generally involves isolating or synthesizing an enantioenriched intermediate whose stereochemistry can be preserved in the required subsequent synthetic transformations.

An example of a useful intermediate in the synthesis of a biologically active molecule is (1R,2R)-1-((tert-butoxycarbonyl)amino)-2-(difluoromethyl)cyclopropanecarboxylic acid (1, Boc-DFAA). In the past, this intermediate was synthesized from (1R,2S)-2 using corrosive fluorination chemistry, which is not suitable for large scale production. WO 2009/064975.

Scheme 1: Synthesis of (1R,2R)-1-((tert-butoxycarbonyl)amino)-2-(difluoromethyl)cyclopropanecarboxylic acid (1) involving corrosive fluorination chemistry

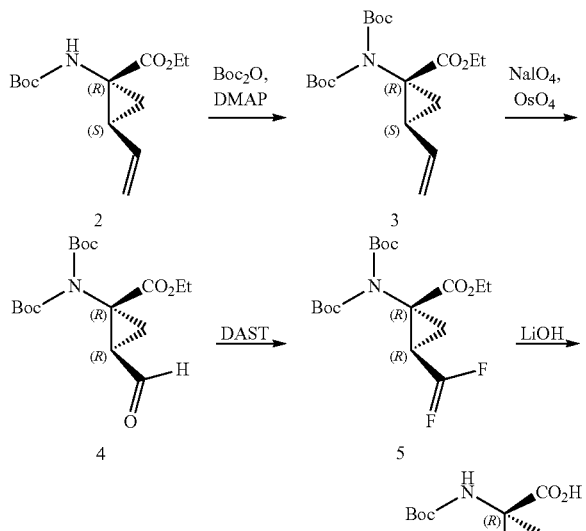

There exists a need for new synthetic methods to construct enantioenriched difluoroalkylcyclopropyl amino esters and their precursors.

SUMMARY OF THE INVENTION

In certain embodiments, the invention relates to a method according to reaction Scheme A:

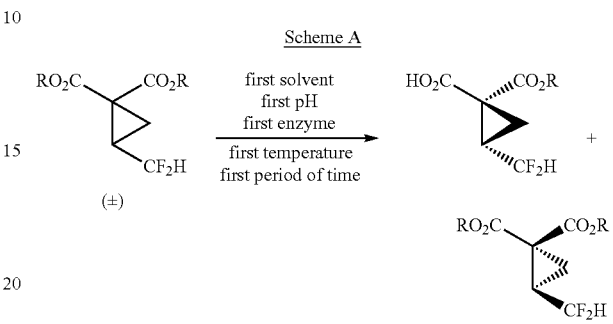

wherein R is alkyl.

In some embodiments, the invention relates to any of the methods described herein, wherein the first solvent is preferably an aqueous solution of sodium citrate or calcium acetate at a concentration of from about 0.05 M to about 0.15 M.

In certain other embodiments, the invention relates to any of the methods described herein, wherein the first enzyme is preferably lipase from *Thermomyces lanuginosus* (AH-45) or (*Rhizo*)*Mucor miehei* (RML).

In certain embodiments, the invention relates to a method according to reaction Scheme B:

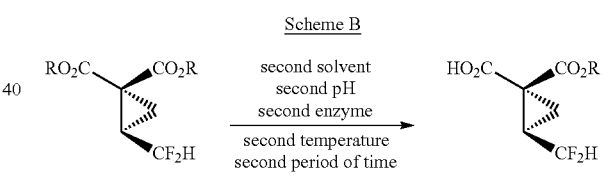

wherein R is alkyl.

In some embodiments, the invention relates to any of the methods described herein, wherein the second solvent is preferably an aqueous solution of sodium phosphate at a concentration of from about 0.05 M to about 0.15 M.

In certain other embodiments, the invention relates to any of the methods described herein, wherein the second enzyme is preferably yvaK esterase or BsteE esterase.

In certain embodiments, the invention relates to a method according to reaction Scheme C:

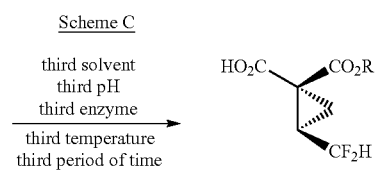

wherein R is alkyl.

In some embodiments, the invention relates to any of the methods described herein, wherein the third solvent preferably comprises an aqueous solution of monopotassium phosphate at a concentration of from about 0.25 M to about 0.75 M.

In certain embodiments, the invention relates to any of the methods described herein, wherein the third solvent further comprises tetrahydrofuran (THF), methyl tert-butyl ether, ethyl acetate, dioxane, DMF, acetonitrile, or DMSO, preferably methyl tert-butyl ether.

In certain other embodiments, the invention relates to any of the methods described herein, wherein the third enzyme is preferably yvaK esterase or BsteE esterase.

In certain embodiments, the invention relates to any of the methods described herein, wherein R is preferably ethyl, propyl, or butyl.

DETAILED DESCRIPTION OF THE INVENTION

I. Overview

In certain embodiments, the invention relates to a method of synthesizing enantioenriched compounds, such as (1S, 2R)-2-(difluoromethyl)-1-(propoxycarbonyl)cyclopropane carboxylic acid (6), by selective enzymatic hydrolysis. The inventive methods are more efficient than known methods because (i) they preferably do not involve synthesizing a racemate and separating enantiomers, and (ii) enantioenriched starting materials are not required.

In certain embodiments, the invention relates to a method of synthesizing a Drug Substance via (1R,2R)-1-((tert-butoxycarbonyl)amino)-2-(difluoromethyl) cyclopropanecarboxylic acid (1) as shown in Scheme 2.

Scheme 2: Structure of (1S,2R)-2-(difluoromethyl)-1-(propoxycarbonyl) cyclopropane carboxylic acid (6), and its conversion to Drug Substance

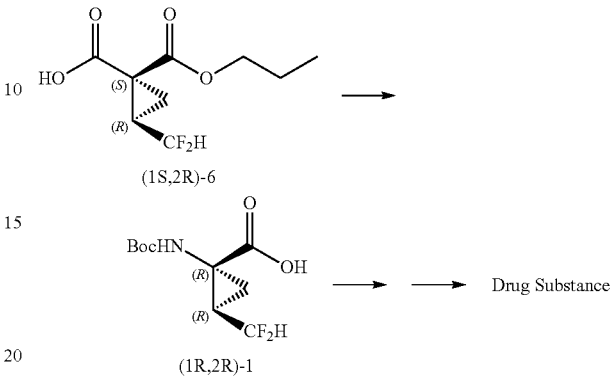

In certain embodiments, the methods of the invention are based on the enzymatic reactive resolution of (±)-dipropyl 2-(difluoromethyl)cyclopropane-1,1-carboxylate (7) followed by enzymatic desymmetrization of the resulting unreacted (R)-diester ((R)-7) to afford (1S,2R)-2-(difluoromethyl)-1-(propoxycarbonyl) cyclopropane carboxylic acid (6), which is isolated as its dicyclohexylamine salt (8), as described in Scheme 3 and Scheme 4.

Scheme 3: Synthesis of (±)-dipropyl 2-(difluoromethyl)cyclopropane-1,1-carboxylate (7)

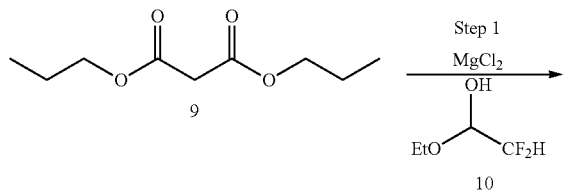

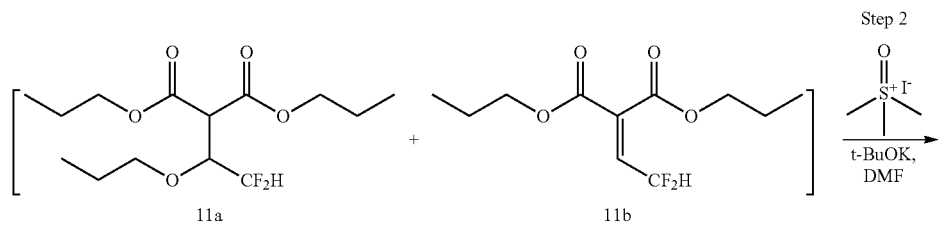

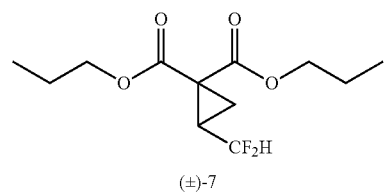

Scheme 4: Enzymatic synthesis of (1S,2R)-2-(difluoromethyl)-1-(propoxycarbonyl)cyclopropane carboxylic acid dicyclohexylamine salt (8)

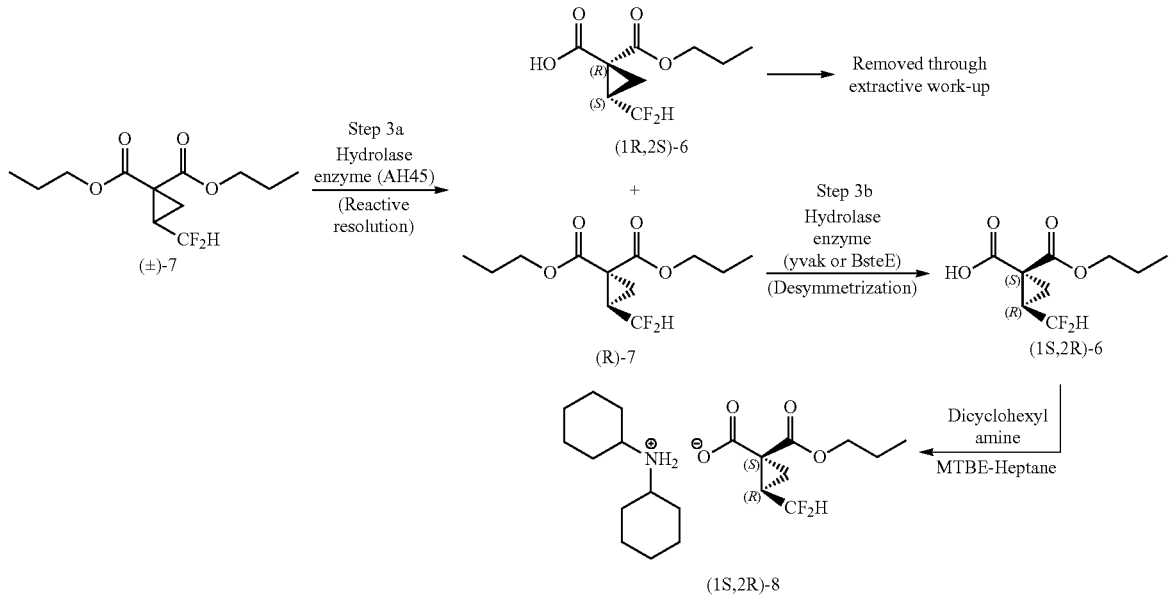

In one embodiment, the (1S,2R)-mono-acid DCHA salt (8) is converted to (1R,2R)-1-((tert-butoxycarbonyl) amino)-2-(difluoromethyl) cyclopropanecarboxylic acid (1, Boc-DFAA) via Curtius Rearrangement followed by hydrolysis, as in Scheme 5.

Scheme 5: Synthesis of (1R,2R)-1-((tert-butoxycarbonyl)amino-2-(difluormethyl)cyclopropanecarboxylic acid (1, Boc-DFAA)

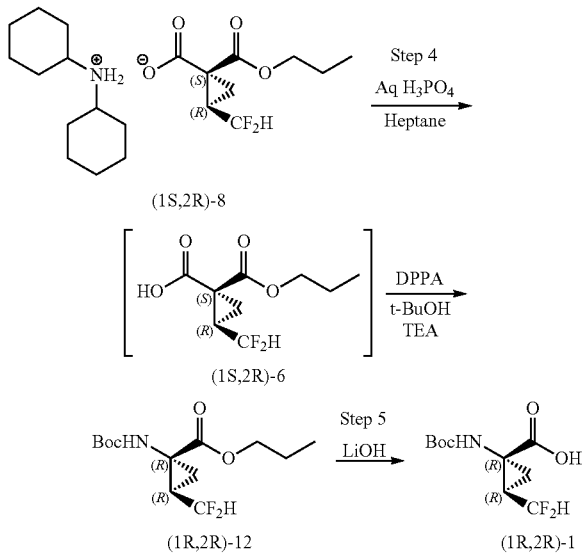

In certain preferred embodiments, the methods do not involve corrosive fluorination reagents or laborious and expensive Simulated Moving Bed (SMB) chromatography for the separation of the desired chiral isomer.

In certain preferred embodiments, the methods improve processability of the isolated intermediates.

Preferably, the overall yield of (1R,2R)-1-((tert-butoxycarbonyl)amino)-2-(difluoromethyl)cyclopropane carboxylic acid (1) is significantly improved as compared to known processes.

II. Definitions

Listed below are definitions of various terms used to describe this invention. These definitions apply to the terms as they are used throughout this specification and claims, unless otherwise limited in specific instances, either individually or as part of a larger group.

The number of carbon atoms in a hydrocarbyl substituent can be indicated by the prefix "$C_x$-$C_y$," where x is the minimum and y is the maximum number of carbon atoms in the substituent.

The term "alkyl" as used herein, refers to a saturated, straight- or branched-chain hydrocarbon radical typically containing from 1 to 20 carbon atoms. For example, "$C_1$-$C_6$ alkyl" or "$C_1$-$C_8$ alkyl" contains from one to six, or from one to eight, carbon atoms, respectively. Examples of alkyl substituents include, but are not limited to, methyl, ethyl, propyl, isopropyl, n-butyl, tert-butyl, neopentyl, n-hexyl, heptyl, octyl substituents and the like.

The term "cycloalkyl" denotes a monovalent group derived from a monocyclic or polycyclic saturated carbocyclic ring compound. Examples of cycloalkyl include, but are not limited to, cyclopropyl, cyclobutyl, cyclopentyl, cyclohexyl, bicyclo[2.2.1]heptyl, and bicyclo[2.2.2]octyl and the like.

The term "amino-protecting group," as used herein, refers to a labile chemical moiety that can protect an amino group against undesired reactions during synthetic procedures. After said synthetic procedure(s), the amino-protecting group as described herein may be selectively removed. Suitable amino-protecting groups are described generally in T. H. Greene and P. G. M. Wuts, Protective Groups in Organic Synthesis, 3rd edition, John Wiley & Sons, New York (1999). Examples of amino-protecting groups include, but are not limited to, t-butoxycarbonyl, 9-fluorenyl-methoxycarbonyl, benzyloxycarbonyl, and the like.

The term "protected amino," as used herein, refers to an amino group protected with an amino-protecting group as defined above.

As used herein, the term "salt" includes "pharmaceutically acceptable salts," which are, within the scope of sound medical judgment, suitable for use in contact with the tissues of humans and other vertebrates, preferably mammals, without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977). Such salts can be prepared in situ during isolation and purification of reaction products as described herein, or separately, such as by reacting a free base function with a suitable acid, such as an organic acid. Examples of pharmaceutically acceptable salts include, but are not limited to, hydrochloride, hydrobromide, phosphate, sulfate, perchlorate, acetate, maleate, tartrate, citrate, succinate, or malonate. Other pharmaceutically acceptable salts include, but are not limited to, adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, sulfate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, ammonium, quaternary ammonium, and amine cations associated with counterions such as halide, hydroxide, carboxylate, sulfate, phosphate, nitrate, alkyl having from 1 to 6 carbon atoms, sulfonate and aryl sulfonate.

As used herein, the term "enantioenriched" means a mixture of enantiomers in which one of the two enantiomers is present in a larger amount (e.g., having an enantiomeric excess (ee) greater than about 90%, greater than about 95%, preferably greater than about 98%, most preferably greater than 99%). This term also encompasses an enantiomerically pure compound.

Various aspects of the invention are described in further detail herein.

III. Exemplary Methods and Uses

The compounds and processes of the present invention will be better understood in connection with the following illustrative methods by which the compounds of the invention may be prepared. It will be understood that any reaction described herein, in any of its variations, can be combined in sequence with one or more of the other reactions described herein, in any of their variations, substantially in analogy with the sequence shown in the Schemes.

In certain embodiments, the invention relates to a method comprising a reactive resolution according to reaction Scheme A:

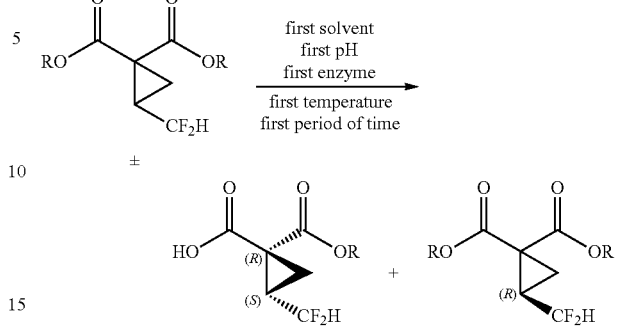

Scheme A wherein R is alkyl.

In certain embodiments, the invention relates to any of the methods described herein, wherein the first solvent is an aqueous buffer, such as an aqueous solution of sodium citrate or calcium acetate, e.g., at a concentration of from about 0.05 M to about 0.15 M, for example, about 0.05 M, about 0.06 M, about 0.07 M, about 0.08 M, about 0.09 M, about 0.10 M, about 0.11 M, about 0.12 M, about 0.13 M, about 0.14 M, or about 0.15 M, preferably about 0.1 M.

In certain embodiments, the invention relates to any of the methods described herein, wherein the first solvent is an aqueous solution of sodium citrate, e.g., at a concentration of from about 0.05 M to about 0.15 M, for example, about 0.05 M, about 0.06 M, about 0.07 M, about 0.08 M, about 0.09 M, about 0.10 M, about 0.11 M, about 0.12 M, about 0.13 M, about 0.14 M, or about 0.15 M, preferably about 0.1 M.

In certain embodiments, the invention relates to any of the methods described herein, wherein the first pH is from about 5 to about 8.5, for example, about 5, about 5.25, about 5.5, about 5.75, about 6, about 6.25, about 6.5, about 6.75, about 7.0, about 7.25, about 7.5, about 7.75, about 8.0, about 8.25, or about 8.5, preferably about 5.75. In certain embodiments, the pH is from about 5 to about 6.5, for example, about 5, about 5.25, about 5.5, about 5.75, about 6, about 6.25, or about 6.5, preferably about 5.75.

In certain embodiments, the invention relates to any of the methods described herein, wherein the first enzyme is a hydrolase, such as a lipase, preferably from *Thermomyces lanuginosus* (AH-45) or *(Rhizo)-Mucor miehiri* (RML). In certain embodiments, the first enzyme is a lipase from *Thermomyces lanuginosus* (AH-45).

In certain embodiments, the invention relates to any of the methods described herein, wherein the loading of the first enzyme is from about 50 wt % to about 150 wt % as compared to the starting material, for example, about 50 wt %, about 60 wt %, about 70 wt %, about 80 wt %, about 90 wt %, about 100 wt %, about 110 wt %, about 120 wt %, about 130 wt %, about 140 wt %, or about 150 wt %, preferably about 100 wt % as compared to starting material.

In certain embodiments, the invention relates to any of the methods described herein, wherein the first temperature is from about 10° C. to about 40° C., for example, about 15° C., about 20° C., about 25° C., about 30° C., about 35° C., or about 40° C., preferably about 20° C.

In certain embodiments, the invention relates to any of the methods described herein, wherein the first period of time is from about 36 h to about 100 h, for example, about 36 h, about 40 h, about 44 h, about 48 h, about 52 h, about 56 h, about 60 h, about 64 h, about 68 h, about 72 h, about 76 h, about 80 h, about 84 h, about 88 h, about 92 h, or about 98 h, preferably about 72 h.

In certain embodiments, the invention relates to any of the methods described herein, further comprising crystallizing the diester reaction product of reaction Scheme A to obtain the diester compound in a crystalline form.

In certain embodiments, the invention relates to any of the methods described herein, further comprising separating the hydrolyzed reaction product of reaction Scheme A from the reaction mixture.

In certain embodiments, the invention relates to any of the methods described herein, further comprising isolating the diester reaction product of reaction Scheme A from the reaction mixture, thereby obtaining substantially pure diester reaction product of Scheme A.

In certain embodiments, the invention relates to any of the methods described herein, wherein the enantiomeric excess of the diester reaction product is greater than about 90%, for example, about 91% ee, about 92% ee, about 93% ee, about 94% ee, about 95% ee, about 96% ee, about 97% ee, about 98% ee, about 99% ee, preferably greater than about 94% ee.

In certain embodiments, the invention relates to a method comprising desymmetrizing a diester according to reaction Scheme B:

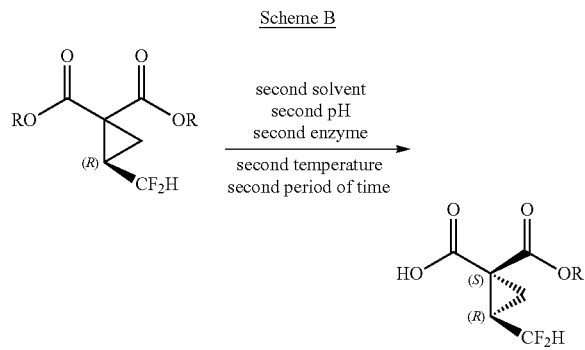

wherein R is alkyl.

In certain embodiments, the invention relates to any of the methods described herein, wherein the second solvent is an aqueous buffer, such as an aqueous solution of sodium phosphate, e.g., at a concentration of from about 0.05 M to about 0.15 M, for example, about 0.05 M, about 0.06 M, about 0.07 M, about 0.08 M, about 0.09 M, about 0.10 M, about 0.11 M, about 0.12 M, about 0.13 M, about 0.14 M, or about 0.15 M, preferably about 0.1 M.

In certain embodiments, the invention relates to any of the methods described herein, wherein the second pH is from about 7.75 to about 9.25, for example, about 8, about 8.25, about 8.5, about 8.75, or about 9, preferably about 8.5.

In certain embodiments, the invention relates to any of the methods described herein, wherein the second enzyme is yvaK esterase, preferably yvaK esterase from *Bacillus subtilis*.

In certain embodiments, the invention relates to any of the methods described herein, wherein the second enzyme is BsteE esterase, preferably BsteE esterase from *Bacillus stearothermophilus*.

In certain embodiments, the invention relates to any of the methods described herein, wherein the second enzyme is provided in a whole cell, such as a freeze-dried whole cell.

In certain embodiments, the invention relates to any of the methods described herein, wherein the loading of the freeze-dried whole cells is from about 40 wt % to about 150 wt % as compared to the starting material, for example, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 100 wt %, about 105 wt %, about 110 wt %, about 115 wt %, about 120 wt %, about 125 wt %, about 130 wt %, about 135 wt %, about 140 wt %, about 145 wt %, or about 150 wt %, preferably about 85 wt % as compared to starting material.

In certain embodiments, the invention relates to any of the methods described herein, wherein the second temperature is from about 10° C. to about 40° C., for example, about 15° C., about 20° C., about 25° C., about 30° C., about 35° C., or about 40° C., preferably about 20° C.

In certain embodiments, the invention relates to any of the methods described herein, wherein the second period of time is from about 10 h to about 30 h, for example, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h, about 25 h, about 26 h, about 27 h, about 28 h, about 29 h, or about 30 h, preferably about 21 h.

In certain embodiments, the invention relates to any of the methods described herein, further comprising isolating the reaction product of reaction Scheme B from the reaction mixture, thereby obtaining substantially pure reaction product of reaction Scheme B.

In certain embodiments, the invention relates to any of the methods described herein, further comprising crystallizing the reaction product of reaction Scheme B to obtain the compound in a crystalline form.

In certain embodiments, the invention relates to any of the methods described herein, further comprising contacting the reaction product of reaction Scheme B with a base to obtain a salt of the compound, optionally in a crystalline form. In some embodiments, the base is an amine, for example, a secondary amine, preferably dicyclohexylamine or dibenzylamine.

In certain embodiments, the invention relates to any of the methods described herein, wherein the enantiomeric excess of the reaction product of reaction Scheme B is greater than about 90%, for example, about 91% ee, about 92% ee, about 93% ee, about 94% ee, about 95% ee, about 96% ee, about 97% ee, about 98% ee, about 99% ee, preferably greater than about 96% ee.

In certain embodiments, the invention relates to any of the methods described herein, wherein the enantiomeric excess of the salt of the reaction product of reaction Scheme B is greater than about 90%, for example, about 91% ee, about 92% ee, about 93% ee, about 94% ee, about 95% ee, about 96% ee, about 97% ee, about 98% ee, about 99% ee, preferably greater than about 97% ee.

In certain embodiments, the invention relates to a method comprising a desymmetrization according to reaction Scheme C:

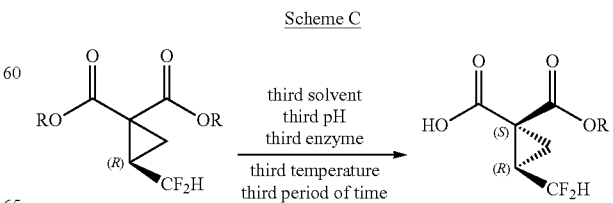

wherein R is alkyl.

In certain embodiments, the invention relates to any of the methods described herein, wherein the third solvent comprises an aqueous buffer, such as an aqueous solution of monopotassium phosphate, e.g., at a concentration of from about 0.25 M to about 0.75 M, for example, about 0.25 M, about 0.3 M, about 0.35 M, about 0.4 M, about 0.45 M, about 0.5 M, about 0.55 M, about 0.6 M, about 0.65 M, about 0.7 M, or about 0.75 M, preferably about 0.5 M.

In certain embodiments, the invention relates to any of the methods described herein, wherein the third solvent further comprises tetrahydrofuran (THF), methyl tert-butyl ether, ethyl acetate, dioxane, DMF, acetonitrile, or DMSO, preferably methyl tert-butyl ether.

In certain embodiments, the invention relates to any of the methods described herein, wherein the third solvent comprises a mixture of an aqueous buffer and an organic solvent.

In certain embodiments, the invention relates to any of the methods described herein, wherein the third pH is from about 6.25 to about 7.75, for example, about 6.5, about 6.75, about 7.0, about 7.25, or about 7.5, preferably about 7.0.

In certain embodiments, the invention relates to any of the methods described herein, wherein the third enzyme is yvaK esterase, such as yvaK esterase from *Bacillus subtilis*.

In certain embodiments, the invention relates to any of the methods described herein, wherein the third enzyme is BsteE esterase, preferably BsteE esterase from *Bacillus stearothermophilus*.

In certain embodiments, the invention relates to any of the methods described herein, wherein the loading of the third enzyme is from about 40 wt % to about 150 wt % as compared to the starting material, for example, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 100 wt %, about 105 wt %, about 110 wt %, about 115 wt %, about 120 wt %, about 125 wt %, about 130 wt %, about 135 wt %, about 140 wt %, about 145 wt %, or about 150 wt %, preferably about 70 wt % as compared to starting material.

In certain embodiments, the invention relates to any of the methods described herein, wherein the third temperature is from about 10° C. to about 40° C., for example, about 15° C., about 20° C., about 25° C., about 30° C., about 35° C., or about 40° C., preferably about 20° C.

In certain embodiments, the invention relates to any of the methods described herein, wherein the second period of time is from about 50 h to about 150 h, for example, about 50 h, about 60 h, about 70 h, about 80 h, about 90 h, about 100 h, about 110 h, about 120 h, about 130 h, about 140 h, or about 150 h, preferably about 100 h.

In certain embodiments, the invention relates to any of the methods described herein, further comprising isolating the reaction product of reaction Scheme C from the reaction mixture, thereby obtaining substantially pure reaction product of reaction Scheme C.

In certain embodiments, the invention relates to any of the methods described herein, further comprising crystallizing the reaction product of reaction Scheme C to obtain the compound in a crystalline form.

In certain embodiments, the invention relates to any of the methods described herein, further comprising contacting the reaction product of reaction Scheme C with a base to obtain a salt of the compound, optionally in a crystalline form. In some embodiments, the base is an amine, for example, a secondary amine, preferably dicyclohexylamine or dibenzylamine.

In certain embodiments, the invention relates to any of the methods described herein, wherein the enantiomeric excess of the reaction product of reaction Scheme C is greater than about 90%, for example, about 91% ee, about 92% ee, about 93% ee, about 94% ee, about 95% ee, about 96% ee, about 97% ee, about 98% ee, about 99% ee, preferably greater than about 98% ee.

In certain embodiments, the invention relates to any of the methods described herein, wherein the enantiomeric excess of the salt of the reaction product of reaction Scheme C is greater than about 90%, for example, about 91% ee, about 92% ee, about 93% ee, about 94% ee, about 95% ee, about 96% ee, about 97% ee, about 98% ee, about 99% ee, preferably greater than about 97% ee.

In certain embodiments, the invention relates to any of the methods described herein, wherein R is ethyl. In other embodiments, R is propyl, such as n-propyl. In yet other embodiments, R is butyl, such as n-butyl.

In certain embodiments, the invention relates to methods comprising two or more of the steps described herein.

In certain embodiments, the invention relates to the use of any of the compounds described herein in the manufacture of a medicament.

Definitions of variables in the structures in the schemes herein are commensurate with those of corresponding positions in the formulae delineated herein.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers. Racemates, and Resolutions (John Wiley & Sons, 1981).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991): L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

EXEMPLIFICATION

The present invention is further illustrated by the following Example which should not be construed as limiting in any way. The Examples and discoveries described herein are representative. As such, the studies and results described in the Examples section herein may be used as a guideline.

Example 1: Knoevenagel Condensation

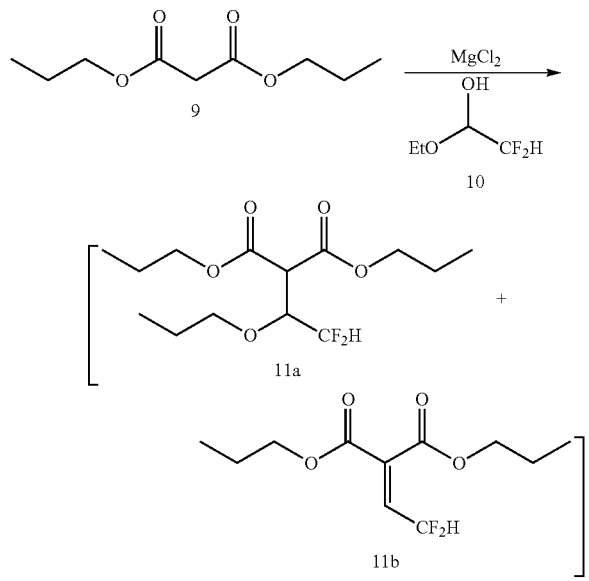

Magnesium chloride (5.06 g, 0.0531 mol, 0.05 equiv.) followed by 1-propanol (600 mL, 3.0 mL/g of dipropyl malonate) were charged to a clean/dry 1.0 L glass reactor under nitrogen, which was set up with a mechanical stirrer and thermocouple at ambient temperature. Agitation was started and difluoroacetaldehyde ethyl hemiacetal (163.77 g, 1.1689 mol, 1.10 equiv., based on 90% potency) was charged and the container was rinsed with 1-propanol (100 mL, 0.5 mL/g of dipropyl malonate). To this mixture, dipropyl malonate (DPM) (200.0 g, 1.0626 mol, 1.00 equiv.) was charged and the flask was rinsed with 1-propanol (100 mL, 0.5 mL/g of dipropyl malonate). The reaction mixture was heated at 60° C. for 46 h and the reaction was deemed completion, as determined by GC analysis of in-process sample [Residual dipropyl malonate: 3.65%, and combined mixture of dipropyl 2-(2,2-difluoro-1-propoxyethyl)malonate (11a) and dipropyl 2-(2,2-difluoroethylidene)malonate (11b): 79.54%]. The mixture was cooled and distilled on a rotary evaporator at NMT 60° C. under vacuum to remove 1-propanol and other volatiles (Bath temp: 60° C.). To the resulting oily residue, MTBE (400 mL) was charged and the distillation was continued under vacuum (Bath temp: 50° C.). MTBE chase distillation was performed two more times (2×400 mL) for a total three times (400 mL MTBE each time) on rotary evaporator (Bath temp: 50° C.). After chase distillations were complete, the resulting oil (383.7 g, hazy solution and contains white solids) was suspended in MTBE (600 mL), mixed for 5 min, filtered and the solid was rinsed with MTBE (200 mL). The combined filtrate was distilled on a rotary evaporator (Bath temp: NMT 50° C.) to afford 351.6 g of dipropyl 2-(2,2-difluoro-1-propoxyethyl)malonate, as a major product, which also contain dipropyl 2-(2,2-difluoroethylidene)malonate as minor product. Purity of the combined mixture by GC: 88.31% and crude product (mixture of dipropyl 2-(2,2-difluoro-1-propoxyethyl)malonate (11a), and dipropyl 2-(2,2-difluoroethylidene)malonate) (11b) used "as is" in cyclopropanation step.

Example 2: Cylopropanation to Form (f)-dipropyl 2-(difluoromethyl)cyclopropane-1,1-carboxylate (7)

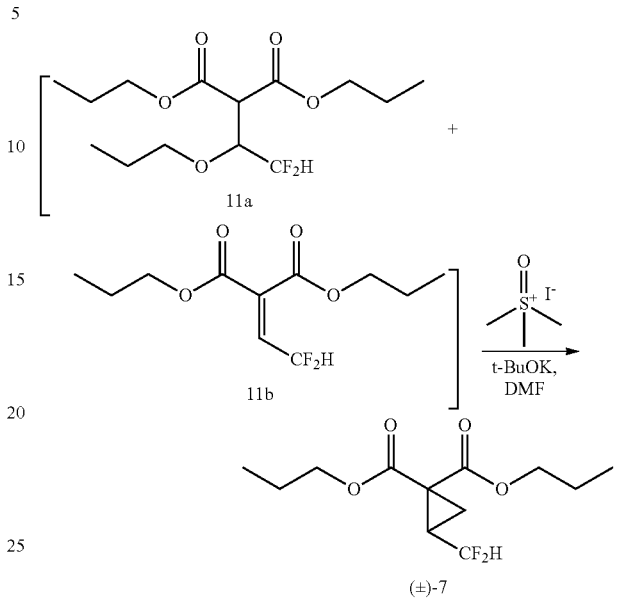

Potassium tert-butoxide (150.6 g, 1.2751 mol, 1.2 equiv.) followed by 1000 mL of DMF were charged under nitrogen into a clean/dry 4 L glass reactor, which was set up with a mechanical stirrer, thermocouple and nitrogen inlet, and the agitation was started. Trimethylsulfoxonium iodide (280.6 g, 1.2751 mol, 1.2 equiv.) was charged and the funnel was rinsed with 400 mL of DMF under nitrogen. The mixture was agitated for 1 h at 20° C. temperature under nitrogen. The crude (dipropyl 2-(2,2-difluoro-1-propoxyethyl)malonate (11a) and dipropyl 2-(2,2-difluoroethylidene)malonate) (11b) was diluted with DMF (150 mL), was charged under nitrogen. The container was rinsed DMF (50 mL) and the mixture was heated at 55° C. for 3 h under nitrogen. Based on GC analysis in-process samples, the reaction was deemed complete with 1.19% of residual dipropyl 2-(2,2-difluoroethylidene)malonate (11b) at 17.28 min and 94.33% of (±)-dipropyl 2-(difluoromethyl)cyclopropane-1,1-carboxylate (7) at 15.29 min. The mixture was cooled to 0-5° C. and the reaction was quenched with water (2.0 L) and MTBE was charged (2.2 L). The temperature of the contents was raised to 20° C. and mixed for 15 min. The aqueous and organic phases were separated and the aqueous phase was back extracted with MTBE two times (1.8 L and 1.0 L). The combined organic phase was washed with 20% sodium chloride soln three times (3×1.25 L), dried with anhydrous magnesium sulfate (50 g), and filtered. The filtrate was concentrated on a rotary evaporator (Bath temp: 55° C.) to afford 278.92 g of (±)-dipropyl 2-(difluoromethyl)cyclopropane-1,1-carboxylate (7), as a yellow/pale red oil with 94.89% (pa) purity by GC.

A portion of the crude (±)-dipropyl 2-(difluoromethyl) cyclopropane-1,1-carboxylate (7, 61.3 g) was purified by flash chromatography (TLC: Hexanes: Rf: 0.2 (Ethyl acetate/10:90, Permanganate strain) on CombiFlash RF system using pre-packed RediSep Rf, Silica column (330 g) and mixture of hexanes and ethyl acetate solvent (90:10) at flow rate of 220 mL/min. The desired fractions were combined (A 16-30, B1-30, C1-30, and D 1-11), and the combined fractions were concentrated on rotary evaporator (Bath temp: 60° C.) and finally chase distilled with hexanes (3×600 mL) on rotary evaporator (Bath temp: 60° C.) to afford 47.9 g (Colorless/clear oil) of (±)-dipropyl 2-(difluoromethyl)cyclopropane-1,1-carboxylate (7) with 97.76% (pa) purity by GC, which used for initial enzyme screening reactions.

Example 3: One-Step Enzymatic Reactive Resolution and Desymmetrization to Form (1S,2R)-2-(difluoromethyl)-1-(ethoxycarbonyl)cyclopropanecarboxylic acid (14, Free Acid)

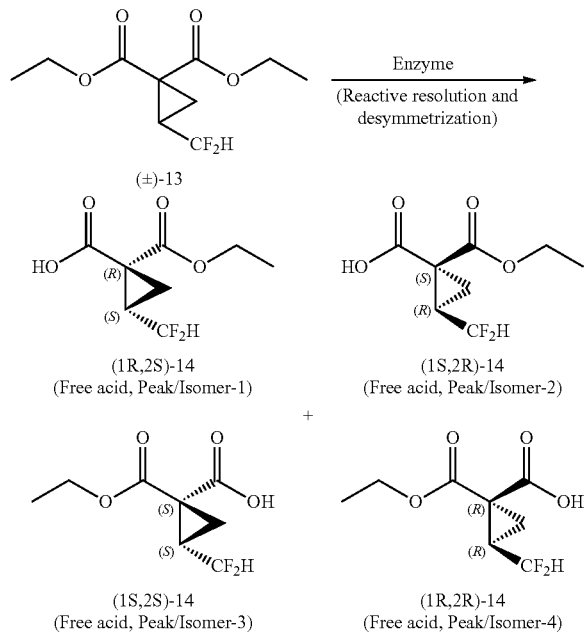

Example 3a: Screen for Enzymes Capable of Reactively Resolving and Desymmetrizing 13

A panel of commerically-available lipases and esterases was screened using chiral HPLC to access their utility in the resolution and desymmetrization of (±)-diethyl diester 13. Fourteen enzymes were evaluated using the following procedure: Enzyme solutions were created by dissolving 5 mg of lyophilized enzyme or 5 μL of liquid enzyme solution into 1 mL of 0.5 M sodium phosphate buffer with 0.2 M sodium chloride at pH 8.0. Diester substrate solution was prepared by combining 18 mg of (±)-diethyl diester 13 per mL of 0.5 M sodium phosphate buffer with 0.2 M sodium chloride at pH 8.0. Reactions were initiated by combining 800 μL of the diester substrate solution with 200 μL of the enzyme solution. The reactions were incubated at 30° C. and 225 rpm for approximately 18 hours. Following incubation, reactions were prepared for chiral HPLC by adding 120 mg sodium chloride and 20 μL of 5 N hydrochloric acid. Two mL of methylene chloride were added to each reaction, and each was vortexed, and centrifuged for 10 minutes at 4000 rpm. The organic layer was decanted and used for HPLC injection. Samples were analyzed on a Chiralpak IC 4.6-mm ID×25-cm column with a Heptane/iPrOH/TFA (98/2/0.1) mobile phase at a flow rate of 1.0 mL/min.

TABLE 1

Enzymatic panel chiral HPLC peak area responses of the selective hydrolysis and desymmetrization of (±)-diethyl diester 13 to 2-(difluoromethyl)-1-(ethoxycarbonyl) cyclopropanecarboxylic acids (14)

| Sample | Enzyme | 8.2 min Diester (S)-13 | 8.5 min Diester (R)-13 | 9.3 min Monoacid (1R,2S)-14 | 9.8 min Monoacid (1S,2R)-14 | 10.8 min Monoacid (1S,2S)-14 | 12.8 min Monoacid (1R,2R)-14 |
|---|---|---|---|---|---|---|---|
| 1 | Lipase - *Rhizomucor miehei* | 73.0 | N/D | 22.7 | <4.4 | N/D | N/D |
| 2 | Esterase - *Bacillus stearathermophilus* | 69.7 | 5.1 | 6.0 | 10.0 | 4.8 | 4.4 |
| 3 | Esterase - Rabbit liver | 24.6 | 2.1 | 36.4 | 25.4 | N/D | 11.5 |
| 4 | Esterase - Porcine liver | 33.7 | 3.1 | 21.8 | 26.8 | 8.5 | 6.1 |
| 5 | PLE Isozyme 1 | 51.0 | 4.9 | 20.1 | 13.0 | 2.7 | 8.3 |
| 6 | PLE Isozyme 2 | 41.3 | 3.5 | 25.5 | 17.6 | 2.8 | 9.4 |
| 7 | PLE Isozyme 3 | 22.5 | 1.9 | 12.2 | 33.9 | 24.5 | 4.9 |
| 8 | PLE Isozyme 4 | 23.8 | 2.0 | 17.5 | 34.1 | 18.1 | 4.5 |
| 9 | PLE Isozyme 5 | 23.7 | 2.4 | 18.1 | 38.5 | 17.3 | N/D |
| 10 | PLE Isozyme 6 | 17.3 | 1.5 | 17.6 | 42.7 | 19.8 | 1.2 |
| 11 | Esterase - *Bacillus subtilis* | 18.2 | 1.6 | 1.8 | 37.7 | 35.9 | 4.6 |
| 12 | Esterase - *Bacillus stearotherrnophilus* | 36.3 | 3.3 | 9.8 | 47.6 | 3.0 | N/D |
| 13 | Esterase - *Paeriibacillus barcinonensis* | 28.6 | 2.6 | N/D | 32.7 | 36.2 | N/D |
| 14 | Esterase - *Pyrobaculum calidifontis* | 41.7 | 3.6 | 11.9 | 7.9 | 4.2 | 30.7 |
| Chemical Hydrolysis | | N/D | N/D | 36.1 | 35.9 | 7.2 | 7.7 |

Example 3b: Preparation of Esterase, "yvaK" Enzyme

An esterase 'yvaK' enzyme from *Bacillus subtilis* was envisioned for selective one step reactive resolution and desymmetrization of (±)-diethyl diester (13) or desymmetrization of (R)-propyl diester (7) due to its high selectivity. The following procedure describes the creation and preparation of 'yvaK' esterase for use as cell-free lysate.

Construction of yvaK Expression Plasmid and Cell Stocks

The following nucleotide sequence was synthesized in pUC57 for use in the subsequent expression of the desired yvaK esterase. Restriction endonuclease sequences of NdeI and BamHI were placed on the respective 5' and 3' ends of the gene sequence for use in ligation to a pET21a expression vector. Alternatively, the restriction digested yvaK gene can be ligated into the pET28a-c expression plasmid using the same procedure. Upon successful ligation into the multiple cloning site of pET21a/pET28a-c at sites NdeI and BamHI, the plasmid was transformed in *E. coli* strain BL21(DE3) competent cells for expression. During the transformation, 2 µL of the plasmid prep was added to competent *E. coli* cells and incubated on ice for 30 min, followed by heat shock at 42° C. for 1 min and back on ice for 2 min. 200 µL of SOC media was added to the transformation mix and incubated at 37° C. for 1 hr. This was plated on pre-warmed LB agar plate containing appropriate antibiotics. The plate was then incubated overnight at 37° C. to allow colonies to form. These colonies were used to inoculate cultures for the subsequent production of cell stocks. Cell stocks were created by mixing equal parts of an overnight (37° C.) culture with pre-sterilized 50:50 $H_2O$:Glycerol and stored at −80° C. until use.

The yvaK esterase gene was restriction digested from the pUC57 vector and ligated into pEt28a using the above procedure and confirmed by colony PCR.

---

*Bacillus subtilis* BS2, yvaK esterase DNA with restriction sites NdeI and BamHI

---

Restriction sites: NdeI, BamHI
Name: BS2_Esterase, aka yvaK
Protein: 246 amino acids, ~32 kDa
Species: *Bacillus subtilis* subsp. *subtilis* str. 168
Gene/insert size: 750 bp
Gene ID: BSU33620

---

Lab-Scale Expression Protocol:

Step 1: Seed inoculum (10 mL) was grow from the yvaK pET21a BL21 (DE3) cell stocks overnight in sterilized Luria Broth (LB) media containing 50 µg/mL ampicillin at 37° C. temperature.

Step 2: Prepare a sterilized, baffled 2 L flask containing 500 mL of LB media with 50 µg/mL ampicillin. Inoculate the flask at 1:200 ratio of overnight seed culture to fermentation broth volume (2.5 mL seed culture per 500 mL fermentation broth)

Step 3: Incubate the fermentation flask at 37° C. and 225 rpm. During this fermentation, periodically monitor the optical density at 600 nm ($OD_{600}$) to determine when the culture has reached the proper growth for induction. It should require approximately 4 hours of incubation to reach the desired $OD_{600}$ of 0.5-0.8 AU. Upon reaching the desired $OD_{600}$, induce the culture by addition of IPTG to a final culture concentration of 0.1 mM.

Step 4: Following induction, adjust the incubation temperature down to 30° C. and 225 rpm, and incubate the culture for 16 hours.

Step 5: Harvest cells by centrifugation for 30 minutes at 3750 rpm and 4° C. Decant and use the resulting cell pellet in preparation of cell-free lysate.

Cell-Free Lysate Preparation:

Step 1: Resuspend cell pellet by vortexing in 0.5 M $K_2HPO_4$ buffer pH 7.0 at a ratio of 1:10 resuspension buffer to original culture volume (50 mL of buffer for a 500 mL-culture pellet).

Step 2: Sonicate the resulting slurry on ice, 3 times for 30 seconds allowing 1 minute intervals in between to cool the culture.

Step 3: Centrifuge lysed cell slurry at 7500 rpm, 4° C. for 20 minutes to remove insoluble cell debris. Decant soluble fraction for use a cell-free lysate.

Fermentation of Esterase Enzyme, yvaK:

A 25 mL starter culture of the esterase enzyme, yvaK, was grown up in LB broth on a shaker at 37° C., 180 RPM in the presence of kanamycin (50 µg mL$^{-1}$) for 7 hrs. Fermentation media was prepared in the 2 L fermenter (working volume 1.5 L) by adding 100 mL of 10× M9 salts (below), 1 mL of autoclaved trace elements (below, autoclave separately), 1 mL of autoclaved magnesium sulfate (1 M, filter sterilized), 1 mL of autoclaved antifoam (propylene glycol) and 1 mL of autoclaved yeast extract (1 g in 10 mL). These components were then added to 30 g of glucose in 100 mL of $H_2O$, which was autoclaved separately.

(SEQ ID NO: 1)

```
CATatgaaagttgtgacaccaaaaccatttacatttaaaggcggagacaaagcggtgcttttgctgcatggctttacaggaaatacagcggatg taaggatgctgggacgatatttgaatgaacgcggctatacgtgccacgcgcctcaatatgaaggacatggcgtcccgcctgaagaacttgtacat acggggcccgaagactggtggaaaaacgtaatggatggctatgaatatttaaaatctgaaggttatgagagcattgctgcctgcggactgtcgctt ggcgggttttttcgctgaaatttgggttacactgtacccataaagggaattgtcccaatgtgcgcaccgatgcatattaagagtgaagaggtcat gtatcaaggcgttctttcatacgctcgcaattacaaaaagtttgaggggaaaagcccggagcaaattgaagaggaaatgaaagaattcgaaaaaac gccgatgaatacccctcaaggcgctgcaagacttaattgctgatgtgcggaataatgtcgatatgatttattcaccgacatttgtggtgcaggcccg tcatgaccacatgattaataccgaaagcgccaatattatttacaacgaagtggaaactgatgataaacagctgaaatggtacgaggaatcagggca tgtcattacactcgacaaagaacgtgacctcgtccatcaggatgtgtatgaatttttagagaagctcgattggtaaGGATCC.
```

| 10 × M9 salts: | |
|---|---|
| Material | Wt |
| Sodium phosphate monobasic, ≥99% | 40 g |
| Potassium phosphate dibasic, ACS reagent, 98% | 146 g |
| Ammonium chloride | 5 g |
| Ammonium sulfate >99% | 25 g |
| Citric acid, 99% | 10 g |
| Sodium sulfate | 20 g |

1 L of water is added to the above ingredients and the mixture is heat sterilized in situ in the fermenter by autoclaving at 121° C. for 30 minutes

| Trace metals: | |
|---|---|
| Material | Wt |
| CaCl$_2$•6 H$_2$O | 0.74 g |
| ZnSO$_4$•7 H$_2$O | 0.18 g |
| MnSO$_4$•H$_2$O, 99% | 0.1 g |
| Citric acid, 99% | 20.1 g |
| FeCl$_3$•6 H$_2$O | 16.7 g |
| CuSO$_4$•5 H$_2$O | 0.1 g |
| CoCl$_2$•6 H$_2$0, 98% ACS reagent | 0.104 g |

1 L of water is added to the above ingredients and the mixture is heat sterilized in situ in the fermenter by autoclaving at 121° C. for 30 minutes The 25 mL starter culture of yvaK was then added to the fermenter. The fermenter was allowed to run at 37° C., with continuous stirring (1200 RPM) with a constant supply of filter-sterilized air from an air pump (initial rate 2 vessel volumes min$^{-1}$). The pH was maintained at pH 7 by addition of 35% v/v solutions of ammonium hydroxide and phosphoric acid, as necessary. After 36 hours, the measured OD$_{600}$ at 36 hours was 17. The glycerol feed was initiated to provide extra nutrients to the growing cells. The components of the glycerol fed are listed below.

| Glycerol feed: | |
|---|---|
| Material | Amount (mL) |
| Glycerol, 99% | 60 mL |
| 10 × M9 salts | 60 mL |
| Magnesium sulfate | 1 mL of 1M solution |
| Trace Metals | 1 mL (Autoclaved separately) |
| Yeast extract, 100 g L$^{-1}$ | 1 mL |

380 mL of water is added to the above ingredients and the mixture is heat sterilized in situ in the fermenter by autoclaving at 121° C. for 30 minutes.
The glycerol was autoclaved separately.

After 44 hours and a measured OD$_{600}$ of 23, the temperature of the fermentation was reduced to 25° C. for protein overexpression. At 45 hours and a measured OD$_{600}$ of 27, the temperature had stabilized at 25° C. Overexpression of the recombinant yvaK enzyme was started by addition of filter sterilized Isopropyl-β-D-1-thiogalactopyranoside (IPTG) to a final concentration of 1 mM. The cells were allowed to continue growing under these conditions overnight for a total fermentation time of 56 hours. At the end of the fermentation, indicated by a rise in dissolved oxygen (DO), the wet cell pellet was collected by centrifugation at 8000 RPM for 10 minutes. A total yield of 51.2 g L$^{-1}$ of wet cell pellet was obtained from the fermentation.

Example 3c: One-Step Enzymatic Reactive Resolution of (±)-diethyl 2-(difluoromethyl)cyclopropane-1,1-carboxylate (13)

In this reaction, yvaK enzyme was prepared as described to yield cell-free lysate of the enzyme. Into an 500 mL Erlenmeyer flask, 210 mL of sodium phosphate buffer was added (0.5 M, pH 6.9), and combined with 15 mL of yvaK cell-free lysate solution. The racemic (±)-diethyl 2-(difluoromethyl)cyclopropane-1,1-carboxylate (13, 750 mg) was added to the flask and set at 30° C. and 125 RPM in a shaker incubator. The reaction was allowed to proceed for 144 hours, and reaction progress was monitored by chiral HPLC. The remaining unreacted diester was removed by twice extracting into 60 mL of methyl tert-butyl ether (MTBE). The remaining aqueous phase was pH adjusted to 3 by the addition of 17 mL of 5 N hydrochloric acid. The monoacid reaction product was recovered by subsequent extraction using three 60 mL fractions of MTBE. The organic fractions were combined and filtered through Celite.

The reaction resulted in 97% conversion of the desired (R)-diester (13) to monoacid isomers (1R,2S)-14:(1S,2R)-14:(1S,2S)-14:(1R,2R)-14 with ratio of with a ratio of isomers 1:2.7:1.25:0 as determined by chiral HPLC, respectively (HPLC elution order: Isomer 1, (1R,2S)-14; Isomer 2 (1S,2R)-14; Isomer 3 (1S,2S)-14; Isomer 4 (1R,2R)-14). From this enzymatic reaction, 81.8% of all monoacid isomers (14) were isolated as a mixture by extraction with MTBE solvent and concentration on a rotary evaporator.

Example 4: Two Step Enzymatic Reactive Resolution and Desymmetrization of (±)-diethyl 2-(difluoromethyl)cyclopropane-1,1-carboxylate (13)

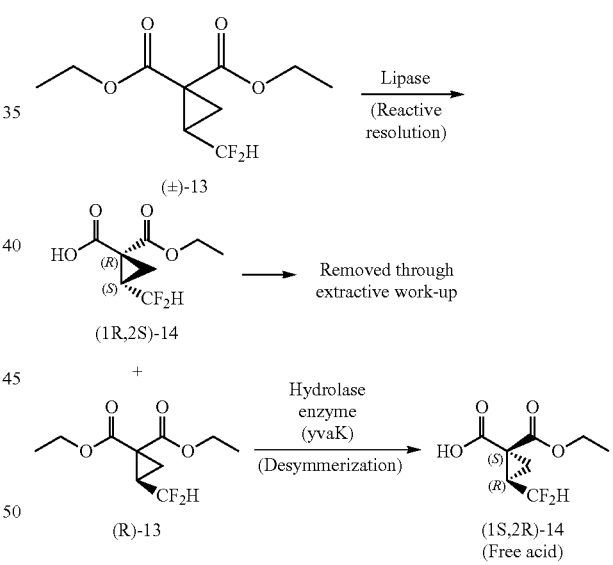

Example 4a: Enzymatic Reactive Resolution of (±)-diethyl 2-(difluoromethyl)cyclopropane-1,1-carboxylate (13)

To a solution of RML (lipase from *Rhizomucor miehei*) (50 mL/g, 27.5 mL) in 0.5 M NaH$_2$PO$_4$ buffer (3.3 g/L total aq. volume, 125 mL) was added a solution of (±)-diethyl 2-(difluoromethyl)cyclopropane-1,1-carboxylate (13, 2.328 mmol, 0.55 g) in DMF (10% v/v, 15 mL). The resulting solution was shaken in an Erlenmeyer flask at 150 rpm at 30° C. for 95 h. The reaction was monitored by chiral HPLC [Regis (S,S)-Whelk O1 5/100 Kromasil 4.6×25 cm, Heptane/i-PrOH/TFA (98/2/0.1], Detector: UV 230 nm] for consumption of (S)-enantiomer of diester (13). The reaction was quenched with brine (50 mL) and saturated NaHCO$_3$ solution and the pH was adjusted to 9. The aqueous reaction solution was extracted with MTBE (3×150 mL); washed combined organic layers with saturated NaHCO$_3$ solution (1×100 mL) and brine (2×100 mL). The undesired (1R,2S)-2-(difluoromethyl)-1-(ethoxycarbonyl) cyclopropanecarboxylic acid (14) remained in aqueous phase and removed. The combined organic layers were dried over excess MgSO$_4$, filtered, and concentrated on a rotary evaporator under vacuum to give the resolved (R)-diethyl 2-(difluoromethyl)cyclopropane-1,1-carboxylate (13) as a pale yellow oil (0.168 g, 97.4% e.e., 64.4% yield).

Example 4b: Enzymatic Desymmetrization of (R)-diethyl 2-(difluoromethyl)cyclopropane-1,1-carboxylate (13)

To a solution of yvaK in 0.5 M NaH$_2$PO$_4$ buffer (5:1 culture vol resuspension, 45 mL) was added (R)-diethyl 2-(difluoromethyl)cyclopropane-1,1-carboxylate (13, 0.635 mmol, 0.15 g). The resulting solution was shaken in an Erlenmeyer flask at 150 rpm at 30° C. for 68 h. The reaction was monitored by chiral HPLC (Regis (S,S)-Whelk O1 5/100 Kromasil 4.6×25 cm, Heptane/iPrOH/TFA [98/2/0.1], UV 230 nm) for consumption of (R)-enantiomer of diester (13). The reaction was quenched with 5N HCl (pH adjust to 2). The aqueous reaction solution was extracted with MTBE (3×60 mL), with centrifugation following each extraction (10 min at 2500 rpm). The combined organic layers were washed with brine (2×50 mL), then dried over excess MgSO$_4$, filtered, and concentrated in vacuo to give (1S,2R)-2-(difluoromethyl)-1-(ethoxycarbonyl)cyclopropanecarboxylic acid (14) as an amber oil (0.109 g, 99.4% e.e., 84.2% yield).

Comparative Example 4a: Separation of (±)-diethyl 2-(difluoromethyl)cyclopropane-1,1-carboxylate (13) enantiomers

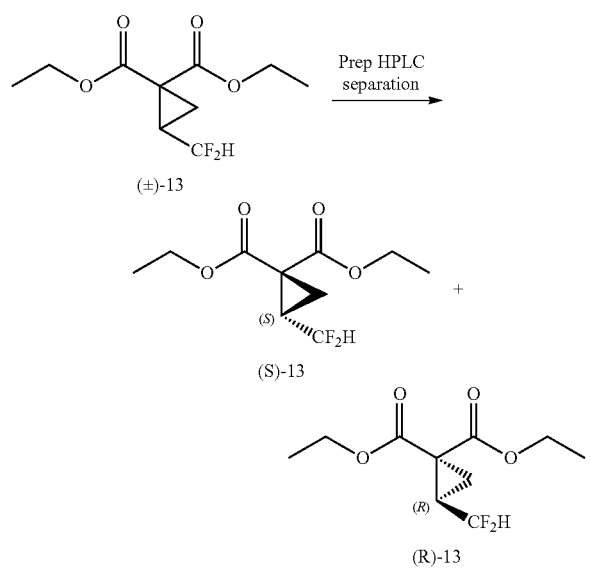

(±)-Diethyl 2-(difluoromethyl)cyclopropane-1,1-carboxylate (13) was dissolved in Heptane/i-PrOH/TFA (98:2:0.1) and made a stock solution with concentration of 40 mg/mL for purification/separation of both enantiomers of 13 by preparative HPLC system (Column: ChiralPak IC, 5µ 21×250 mm; Mobile Phase: Heptane/i-PrOH/TFA (98/2/0.1), Solvent system: Isocratic; Detector: UV 215 nm, Column temperature: Ambient, 19-23° C.; Injection Volume: 2 mL, Run time: 20 min). Both (R) and (S)-enantiomers of 13 were collected in two fractions and the combined fractions concentrated on a rotary evaporator under vacuum to afford 0.94 g of Isomer 1, (S)-diethyl 2-(difluoromethyl)cyclopropane-1,1-carboxylate ((S)-13, Isomer 1) in >99.5% e.e., and 0.89 g of Isomer 2, (R)-diethyl 2-(difluoromethyl)cyclopropane-1,1-carboxylate ((R)-13, Isomer 2) in >99.5% e.e.

Example 5: Enzymatic Reactive Resolution Screening of (±)-dimethyl 2-(difluoromethyl)cyclopropane-1,1-carboxylate (15), (±)-dipropyl 2-(difluoromethyl)cyclopropane-1,1-carboxylate (7) and (±)-dibutyl 2-(difluoromethyl)cyclopropane-1,1-carboxylate (17)

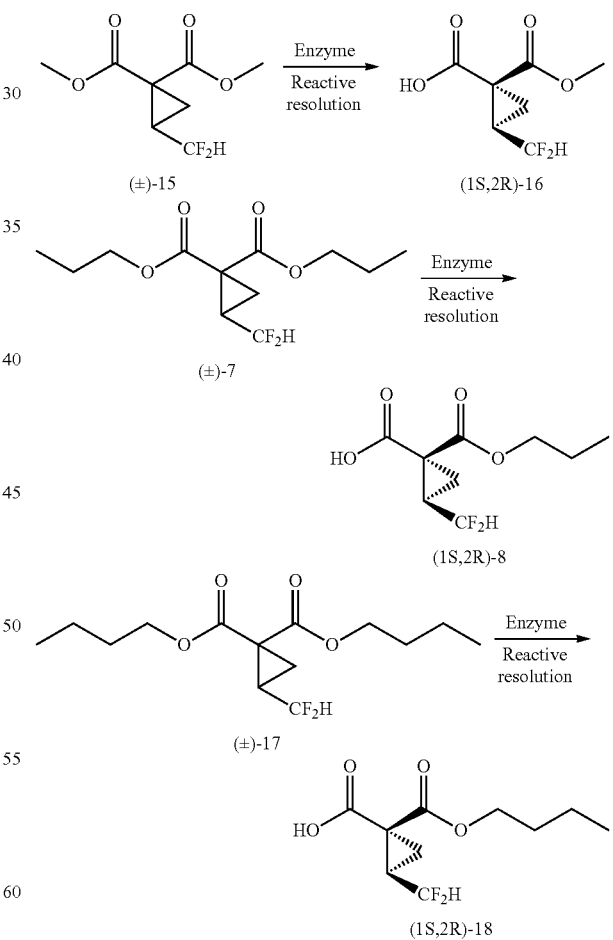

A range of esters were synthesized as alternatives to the ethyl diester (13) (Example 4) to ascertain if increases in selectivity could be achieved. Racemic methyl (15), propyl (7) and butyl (17) diesters were synthesized for evaluation in the hydrolysis reaction of racemic diester. Several enzymes; AH-45, AH-46, and DSM PLE 444 showed improvements in selectivity during preliminary screening were evaluated for their applicability.

Example 5a: Methyl Diester (15)

Screening of methyl diester (15) yielded a number of potential enzymes which were screened for their selectivity in diester hydrolysis. The results of this optimization are detailed in the following section.

DSM PLE 444 Mediated Desymmetrization of Methyl Diester (15)

DSM PLE 444 was identified as a potential enzyme to deliver the required (1S,2R)-monoacid product directly. Reactions were carried out over a range of pH's to determine if the E-value could be improved sufficiently to make this a viable option. The reaction at pH 6 gave the highest selectivity toward the desired monoacid by the following procedure.

To a 3-neck 50 mL round bottomed flask, $KH_2PO_4$ buffer (0.1 M, 20 mL) was charged. Enzyme DSM PLE 444 was charged followed by addition of substrate (100 mg). The reactions were stirred at 1000 rpm with magnetic fleas. The reactions were allowed to run overnight and worked up for analysis. The pH was adjusted to 1.85 by addition of 2 M HCl. The aqueous was extracted with MTBE (2×10 mL). The combined organics were concentrated in vacuo, taken up in 95/5 heptane/EtOH, filtered through $MgSO_4$ and concentrated.

AH-45 Mediated Resolution of Methyl Diester (15)

To a COC vial, 0.1 M $KH_2PO_4$ buffer (pH 6, 10 mL) was charged. Enzyme AH-45 (50 µL) was charged followed by addition of dimethyl ester substrate (15, 50 mg). The reactions were shaken at 200 RPM for 20 hours, and then worked up by adjusting the pH to 1.85 by addition of 2 M HCl. The aqueous was extracted with MTBE (2×10 mL). The emulsion was filtered through Celite, which was washed with MTBE. The combined organics were concentrated in vacuo, taken up in 95/5 hep/EtOH, filtered through $MgSO_4$ and concentrated.

Example 5b: Propyl Diester (7)

Screening of propyl diester (7) yielded a number of potential enzymes which were screened for their selectivity in diester hydrolysis. The results of this optimization are detailed in the following section.

AH-45 Mediated Resolution of Propyl Diester (7)

To a COC vial, 0.1 M $KH_2PO_4$ buffer (pH 7, 10 mL) was charged. Enzyme AH-45 (50 µL) was charged followed by addition of dipropyl ester substrate (7, 50 mg). The reactions were shaken at 200 RPM for 20 hours, and then worked up by adjusting the pH to 1.85 by addition of 2 M HCl. The aqueous was extracted with MTBE (2×10 mL). The emulsion was filtered through Celite, which was washed with MTBE. The combined organics were concentrated in vacuo, taken up in 95/5 hep/EtOH, filtered through $MgSO_4$ and concentrated. This reaction was carried out in the $Ca(OAc)_2$ buffer and the rate of reaction was improved significantly.

AH-46 Mediated Resolution of Propyl Diester (7)

To a COC vial, 0.1 M $KH_2PO_4$ buffer (pH 7, 10 mL) was charged. Enzyme AH-46 (50 µL) was charged followed by addition of dipropyl ester substrate (7, 50 mg). The reactions were shaken at 200 RPM for 20 hours, and then worked up by adjusting the pH to 1.85 by addition of 2 M HCl. The aqueous was extracted with MTBE (2×10 mL). The emulsion was filtered through Celite, which was washed with MTBE. The combined organics were concentrated in vacuo, taken up in 95/5 hep/EtOH, filtered through $MgSO_4$ and analyzed by HPLC.

Example 5c: Butyl Diester (17)

Screening of butyl diester (17) yielded a number of potential enzymes which were screened for their selectivity in diester hydrolysis. The results of this optimization are detailed in the following section.

AH-45 Mediated Resolution of Butyl Diester (17)

To a COC vial, 0.1 M $KH_2PO_4$ buffer (pH 7, 10 mL) was charged. Enzyme AH-45 (50 µL) was charged followed by addition of dibutyl ester substrate (17, 50 mg). The reactions were shaken at 200 RPM for 20 hours, and then worked up by adjusting the pH to 1.85 by addition of 2 M HCl. The aqueous was extracted with MTBE (2×10 mL). The emulsion was filtered through Celite, which was washed with MTBE. The combined organics were concentrated in vacuo, taken up in 95/5 hep/EtOH, filtered through $MgSO_4$ and concentrated AH-46 Mediated Resolution of Butyl Diester (17)

To a COC vial, 0.1 M $KH_2PO_4$ buffer (pH 8, 10 mL) was charged. Enzyme AH-46 (50 µL) was charged followed by addition of dibutyl ester substrate (17, 50 mg). The reactions were shaken at 200 RPM for 20 hours, and then worked up by adjusting the pH to 1.85 by addition of 2 M HCl. The aqueous was extracted with MTBE (2×10 mL). The emulsion was filtered through Celite, which was washed with MTBE. The combined organics were concentrated in vacuo, taken up in 95/5 hep/EtOH, filtered through $MgSO_4$ and concentrated.

Example 6: Enzymatic Reactive Resolution and Desymmetrization to Form (1S,2R)-2-(difluoromethyl)-1-(propoxycarbonyl)cyclopropanecarboxylic acid dicyclohexylamine salt (8)

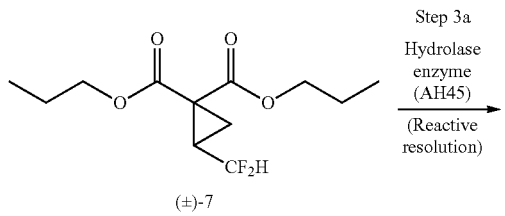

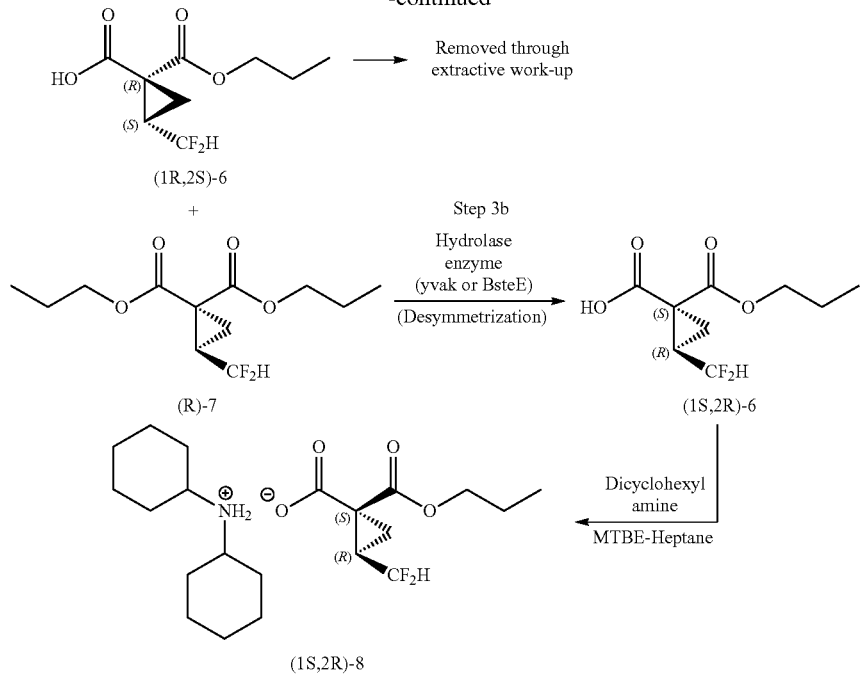

Example 6a: Enzymatic Reactive Resolution of (±)-dipropyl 2-(difluoromethyl)cyclopropane-1,1-carboxylate (7) via AH-45

0.1 M sodium citrate buffer, pH 5.75 (800 mL, 40 vol) was charged to a 3-neck 2-L RBF equipped with a calibrated pH probe, pH stat addition line, baffle and a mechanical stirrer. The reaction mixture was warmed to 20° C. before AH-45 (20 g, 100 wt % wrt substrate) was added. Crude (±)-dipropyl 2-(difluoromethyl)cyclopropane-1,1-carboxylate (7) (20 g) was subsequently added and the reaction was stirred at 400 rpm.

Samples (2 mL) were removed, adjusted to acidic pH by addition of 10 drops of 2 M HCl, then extracted with MTBE (2 mL). The organic layer was concentrated in vacuo, then the residue was taken up in 95/5 (v/v) Hex/EtOH (1 mL) which was dried over $Na_2SO_4$ and analyzed on HPLC.

After 72 h the reaction had reached 94% diester ee and was worked up. The reaction pH was adjusted to pH 8.4 by addition of 15% (w/w) $Na_2CO_3$ solution. The reaction mixture was extracted with MTBE (2×100 mL). The emulsified organic layers were transferred to falcon tubes and centrifuged at 10000 g for 10 mins. The MTBE layers were decanted off, combined, washed with sat. bicarb (40 mL) and water (40 mL). The organic layer was then concentrated in vacuo to give 7 as a yellow oil (7.58 g, 94.8% e.e., 96% wt/wt by 1H NMR assay). Expected yield=9.4 g, Recovered=7.27 g (corrected for assay), % yield=77.

Example 6b(i): Desymmetrization of (R)-dipropyl 2-(difluoromethyl)cyclopropane-1,1-carboxylate ((R)-7) Via yvaK 0.1 M sodium phosphate buffer, pH 8.5 (290 mL) was charged to a 3-neck 1-L RBF equipped with a calibrated pH probe, pH stat addition line, baffle and a mechanical stirrer. The reaction mixture was warmed to 20° C. before yvaK freeze dried whole cells (6.3 g, 86 wt % wrt substrate) was added. The pH was then re-adjusted to 8.5. (R)-cyclopropyl diester 7 (7.58 g, 94.8% e.e., 96% purity by 1H NMR assay) in MTBE (7.6 mL) was subsequently added and the reaction was stirred at 400 rpm.

Samples were taken periodically to check reaction progress. The analysis was performed using the achiral method. A sample of the reaction mixture (0.5 mL) was diluted with EtOH (0.5 mL) and THF (0.25 mL). The sample was then centrifuged at 13200 rpm for 2 mins. The supernatant was removed and filtered through a 0.2 μm filter. The sample was then analyzed directly on HPLC.

After 21 h reaction was deemed complete. The pH was adjusted to 1.5 by addition of 20% HCl solution. Toluene (40 mL) was added followed by Celite (6.3 g) and the reaction mixture stirred for 30 mins. The suspension was then filtered on a sintered funnel (filtration slow, Celite resembled chewing gum). The filtrate was transferred to separating funnel, and the toluene layer was separated off. The Celite was rinsed with toluene (40 mL) which was then used for 2nd extraction of the aqueous layer. The Celite cake was then transferred to a flask and slurried overnight with MTBE (100 mL). Concentration of MTBE layer yielded a red oil (2.4 g).

Following on from the DCHA salt screening reactions it was deemed that salt formation would be carried out in MTBE/Heptane as solvent/antisolvent. The toluene layer was combined with the residue from the MTBE layer and concentrated in vacuo. The residue was azeodried from toluene (2×150 mL), then the residue was taken up in MTBE (50 mL), filtered to remove solid particles and concentrated to afford (1S,2R)-7 as a reddish oil (4.04 g, 96.8% e.e., 89% purity by $^1$H NMR assay).

Example 6b(ii): Desymmetrization of (R)-dipropyl 2-(difluoromethyl)cyclopropane-1,1-carboxylate ((R)-7)

In the following procedure, a one-step resolution of enriched (R)-dipropyl ester (7) was performed to yield (/S,2R)-monoacid as the major product species. In this reaction, a 500 mL culture pellet of yvaK enzyme was resuspended in 25 mL of $KH_2PO_4$ buffer (0.5 M pH 7.0). The resuspension was sonicated 3 times in 30 second intervals over ice. The lysate solution was then centrifuged at 7500 RPM, 4° C. for 15 minutes, and the supernate was retained as the cell-free lysate solution. To this solution of yvaK in 0.5M $KH_2PO_4$ buffer (0.035 g [71% wt/wt], 13.4 mL) was added a solution of enriched (R)-dipropyl ester (9, 0.189 mmol, 0.050 g) in MTBE (3.33 mL/g, 0.17 mL). The resulting opaque solution stirred vigorously at room temperature (22° C.) for 98h. Reaction mixture was quenched with 5N HCl (pH adjust to <2), then extracted with MTBE (2×10 mL), with centrifugation following each extraction (10 min at 2500 RPM). The combined organic layers were dried over excess $MgSO_4$, filtered, and concentrated in vacuo (35° C. water bath) to give (/S,2R)-monoacid ((1S, 2R)-6, 0.0422 g) as an amber oil [crude] (98.8% e.e., 97% wt/wt by $^1$H-NMR, 97% recovery).

Example 6c: Formation of (1S,2R)-2-(difluoromethyl)-1-(propoxycarbonyl)-cyclopropanecarboxylic acid dicyclohexylamine salt (8)

Monoacid (1S,2R)-6 (4.04 g, 96.8% e.e., 89% assay by NMR), prepared as described in Example 6b(i), was dissolved in MTBE (3.6 mL, 1 vol) with stirring. DCHA (3.00 g, 1 eq) was added in slowly to the solution. As heptane (22 mL) was about to be added, the DCHA salt spontaneously crystallised from solution to give a solid mass. Heptane was added and the solid broken up and stirred for 1 h. The solid was filtered; however the solid contained fine white solid and brown coloured lumps. The solid was transferred to a flask and slurried in MTBE (10 mL) for 1 h, then filtered to leave a white solid which was dried on the filter (3.3 g). Yield too low. The solids and filtrates were combined and concentrated, then the solid was taken up in MTBE (3.6 mL) and heated to 40° C. to give a mobile slurry. Heptane (22 mL) warmed to 40° C. was then added to the suspension and was stirred for 2 h. The suspension was allowed to cool to room temperature overnight. The suspension was then filtered and dried on the filter to afford (1S,2R)-8 as a white solid (4.0 g, 98.0% e.e.).

Example 6d: Enzymatic Reactive Resolution of (±)-dipropyl 2-(difluoromethyl)cyclopropane-1,1-carboxylate (7) via AH-45

0.1 M calcium acetate buffer, pH 7.5 (265 mL, 10.6 vol) was charged to a 500-mL RBF equipped with a calibrated pH probe, pH stat addition line, temperature probe and mechanical stirrer. To the buffer solution were charged AH-45 (12.5 g, 50 wt %) and crude (±)-dipropyl 2-(difluoromethyl)cyclopropane-1,1-carboxylate ((±)-7, 25 g). The reaction was stirred at 300 rpm, controlled at 19-24° C., and monitored by chiral HPLC [Phenomenex Lux 3 μm Cellulose-2, 250×4.6 mm, Heptane/i-PrOH/TFA (98.5/1.5/0.1], Detector: UV 210 nm].

After 90 h, the reaction had reached 99.8% diester e.e. and was adjusted to pH 1.5 by addition of 20% (w/w) HCl solution. Celite (6.7 g, 25 wt %) was added to the reaction mixture and stirred, followed by MTBE (50 mL, 2 vol) and stirred. The biphasic mixture was filtered and the filter cake was rinsed with MTBE (3×50 mL). The resulting organic filtrate was used to extract the aqueous. The organic phases were combined and washed with 5% (w/w) sodium bicarbonate solution (3×50 mL), dried over $MgSO_4$, filtered, and concentrated in vacuo to give (R)-7 as a dark yellow oil (9.50 g, 99.6% e.e., 93.3 wt % by qNMR assay). Expected yield=10.95 g, Recovered=8.86 g (corrected for assay), % yield=82.

Example 6e: Desymmetrization of (R)-dipropyl 2-(difluoromethyl)cyclopropane-1,1-carboxylate ((R)-7) via BsteE 0.1 M sodium phosphate buffer, pH 8.3 (117 mL, 14 vol) was charged to a 500 mL RBF equipped with a pH probe, pH stat addition line, temperature probe and mechanical stirrer. The solution was controlled at 45-50° C. before charging BsteE pretreated cell lysate solution (30 mL, 3.57 vol) followed by (R)-cyclopropyl diester (R)-7 (8.4 g crude, 7.8 g assay adjusted, 99.6% e.e.), prepared as described in example 6d. The reaction was stirred at 400 rpm, controlled at 45-50° C., and monitored by chiral HPLC.

After 24 h, the reaction had reached >99 PA % monoacid (wrt diester) and was cooled to 19-24° C., pH was adjusted to 1.5 by addition of 20% (w/w) HCl solution, and diluted with MTBE (50 mL, 6 vol). The biphasic mixture was filtered and the filter cake was rinsed with MTBE (2×50 mL). The resulting organic filtrate was used to extract the aqueous. The organic phases were combined and washed with purified water (50 mL), dried over $MgSO_4$, filtered, and concentrated in vacuo to give (1S,2R)-6 as a dark yellow oil (6.79 g, 99.3% e.e., 93.7 wt % by qNMR assay). Expected yield=6.59 g, Recovered=6.36 g (corrected for assay), % yield=97.

Example 6f: Formation of (1S,2R)-2-(difluoromethyl)-1-(propoxycarbonyl)-cyclopropanecarboxylic acid dicyclohexylamine salt (8)

Monoacid (1S,2R)-6 (1.09 g crude, 1.02 g assay adjusted, 99.3% e.e.), prepared as described in Example 6e, was charged to a 25 mL flask equipped with stir bar, followed by MTBE (1.1 mL, 1 vol) and n-heptane (6.6 mL, 6 vol). The mixture was heated to 40-45° C. and mixed until (1S,2R)-6 dissolved completely. Dicyclohexylamine (0.96 mL, 1 eq) was added slowly dropwise to the reaction solution. The reaction slurry was held at temperature and mixed for 1 h, then cooled to ambient temperature (19-24° C.) and mixed for 16 h. The reaction slurry was subsequently cooled to 5-10° C. and held at temperature for 6 h, then filtered. The filter cake was washed with a 6:1 n-heptane:MTBE solution (2×1 mL), then dried in a vacuum oven (35-40° C., 35-65 torr) for 16 h, to afford (1S,2R)-8 as a white solid (1.42 g, 99.9% e.e., 98.2 wt % by qNMR assay). Expected yield=1.77 g, Recovered=1.39 g (corrected for assay), % yield=79.

Example 7: Curtius Rearrangement to Form (1R, 2R)-propyl 1-((tert-butoxycarbonyl) amino)-2-(difluoromethyl)cyclopropanecarboxylate (12)

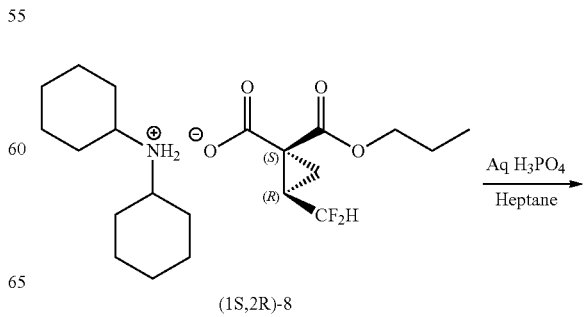

(1S,2R)-8

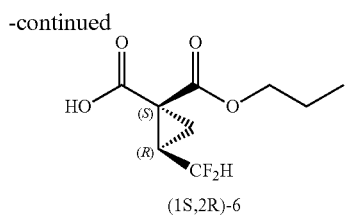

(1S,2R)-6

Example 7a: Salt Break

A 100-mL round bottom flask, equipped with a Teflon coated magnetic stirbar, was charged with the above dicyclohexylamine salt (1S,2R)-8 (4.0 g, 9.91 mmol) and MTBE (30 mL). To this suspension was added a 15% $H_3PO_4$ solution (w/w, 18 mL) and the resulting mixture was stirred at room temperature for 15 min. The resulting solution was poured into a 125-mL separatory funnel and the layers were cut. The top organic layer was washed with an additional 2.5 mL 15% $H_3PO_4$ and the layers cut. The organic layer was then washed with sat. aq. NaCl, the layers cut, and the organics dried over $MgSO_4$. After filtration of the $MgSO_4$, the solvent was removed in vacuo to give 2.54 g free acid (1S,2R)-6 as a clear oil.

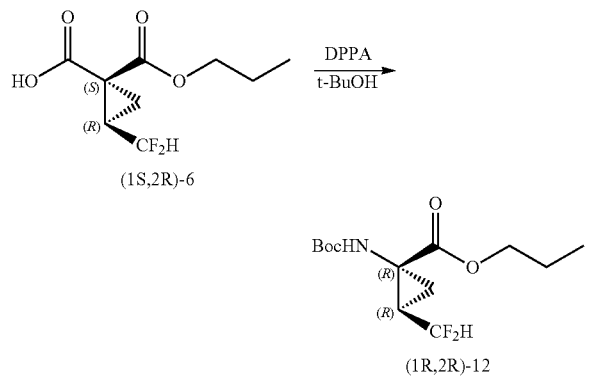

Example 7b: Curtius Rearrangement

A separate 100-mL three-necked flask equipped with a mechanical stirrer and pressure equalizing addition funnel, was charged with t-BuOH (16.6 mL), free acid (1S,2R)-6 (2.54 g, 11.43 mmol), triethylamine (5.26 g, 7.25 mL, 52.02 mmol). The mixture was then heated to 80-84° C. (bath temperature). DPPA (2.43 g, 1.9 mL, 8.82 mmol) was added slowly using a syringe pump, and the mixture was allowed to stir for an additional NLT 6 hours after complete addition. The solvent removed under reduced pressure and the crude oil was dissolved in 60 mL MTBE and added to a separatory funnel. The organic phase was first washed with 5% citric acid (2×30 mL) and the layers cut. The organic phase was then washed with sat. aq. $NaHCO_3$ (2×30 mL) and the layers cut. The organics were then washed with $H_2O$ (2×30 mL) and the layers cut. The organic phase was dried over $Na_2SO_4$, filtered, and concentrated to provide 2.45 g of (1R,2R)-propyl 1-((tert-butoxycarbonyl)amino)-2-(difluoromethyl)cyclopropanecarboxylate (12) as a yellow-orange oil, which was used as is in next step.

Example 8: Hydrolysis to Form (1R,2R)-1-((tert-butoxycarbonyl)amino)-2-(difluoromethyl)cyclopropane carboxylic acid (1)

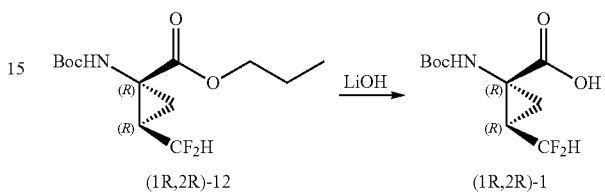

A solution of (1R,2R)-propyl 1-((tert-butoxycarbonyl)amino)-2-(difluoromethyl)cyclopropanecarboxylate (12) (2.43 g, 8.28 mmol), prepared as described above, in acetonitrile (13 mL) was cooled to 5° C., then treated with a solution of LiOH (0.60 g, 24.85 mmol, 3.0 equiv) in water (13 mL), added over 7 minutes. The mixture was stirred at ambient temperature overnight. Upon reaction completion, 15% aqueous citric acid was added to achieve a pH of 4-4.5. The mixture was concentrated under vacuum to remove the acetonitrile, and solid NaCl was added to make a saturated solution. The resulting slurry was mixed overnight at ambient temperature, filtered and washed with 2 mL water to afford 7.5 g of wet cake, which was crystallized from water and dried in a vacuum oven to afford 1.1 g of (1R,2R)-1-((tert-butoxycarbonyl)amino)-2-(difluoromethyl)cyclopropanecarboxylic acid (1).

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents, and published patent applications, and patent applications cited throughout this application are incorporated herein by reference.

We claim:

1. A method according to reaction Scheme A:

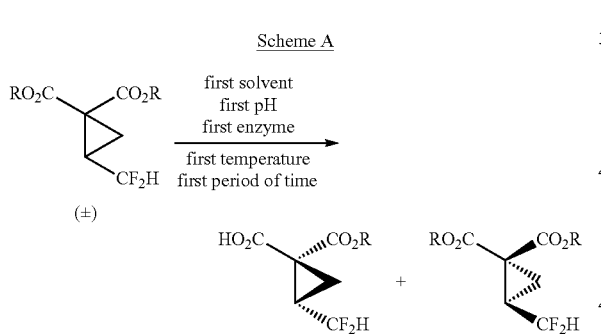

wherein R is alkyl; and
the first enzyme is a lipase or an esterase.

2. The method of claim 1, wherein the first solvent is an aqueous solution of sodium citrate or calcium acetate.

3. The method of claim 1, wherein the first pH is from 5 to 8.5.

4. The method of claim 1, wherein the first enzyme is *Thermomyces lanuginosus* lipase (AH-45) or (*Rhizo-*)*Mucor miehei* lipase (RML).

5. The method of claim 1, wherein

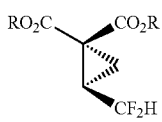

has an enantiomeric excess of greater than 90%.

6. A method according to reaction Scheme B:

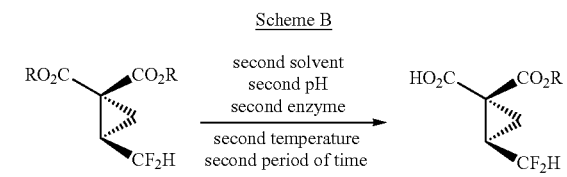

wherein R is alkyl; and
the second enzyme is yvaK esterase or BsteE esterase.

7. The method of claim 1, further comprising the step of reaction Scheme B:

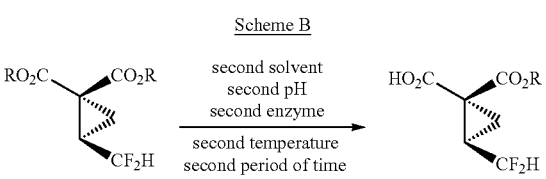

wherein R is alkyl; and
the second enzyme is yvaK esterase or BsteE esterase.

8. The method of claim 7, wherein the second solvent is an aqueous solution of sodium phosphate.

9. The method of claim 7, wherein the second pH is from 7.75 to 9.25.

10. The method of claim 7, wherein the second enzyme is provided in a whole cell, and optionally the whole cell is freeze-dried.

11. The method of claim 7, wherein
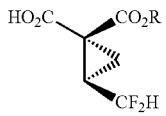
has an enantiomeric excess of greater than 90%.
12. The method of claim 7, further comprising contacting the reaction product of reaction Scheme B with a base to obtain a salt of the compound.
13. The method of claim 12, wherein the base is dicyclohexylamine or dibenzylamine.
* * * * *

SEQUENCE LISTING

<160> NUMBER OF SEQ ID NOS: 1

```
<210> SEQ ID NO 1
<211> LENGTH: 750
<212> TYPE: DNA
<213> ORGANISM: Bacillus subtilis

<400> SEQUENCE: 1
catatgaaag ttgtgacacc aaaaccattt acatttaaag gcggagacaa agcggtgctt      60
ttgctgcatg gctttacagg aaatacagcg gatgtaagga tgctgggacg atatttgaat     120
gaacgcggct atacgtgcca cgcgcctcaa tatgaaggac atggcgtccc gcctgaagaa     180
cttgtacata cggggcccga agactggtgg aaaaacgtaa tggatggcta tgaatattta     240
aaatctgaag gttatgagag cattgctgcc tgcggactgt cgcttggcgg ggtttttcg      300 ctgaaattgg gttacactgt acccataaag ggaattgtcc caatgtgcgc accgatgcat     360
attaagagtg aagaggtcat gtatcaaggc gttctttcat acgctcgcaa ttacaaaaag     420 tttgaggga aaagcccgga gcaaattgaa gaggaaatga agaattcga aaaaacgccg       480 atgaataccc tcaaggcgct gcaagactta attgctgatg tgcggaataa tgtcgatatg     540
atttattcac cgacatttgt ggtgcaggcc cgtcatgacc acatgattaa taccgaaagc     600
gccaatatta tttacaacga agtggaaact gatgataaac agctgaaatg gtacgaggaa     660
tcagggcatg tcattacact cgacaaagaa cgtgacctcg tccatcagga tgtgtatgaa     720
tttttagaga agctcgattg gtaaggatcc                                      750
```